United States Patent [19]

Konz et al.

[11] Patent Number: 4,590,273

[45] Date of Patent: May 20, 1986

[54] ISOQUINOLINE COMPOUNDS

[75] Inventors: Elmar Konz, Kelkheim; Franz Hock, Dieburg; Joachim Kaiser, Frankfurt am Main; Hansjörg Kruse, Kelkheim, all of Fed. Rep. of Germany

[73] Assignee: Hoechst Aktiengesellschaft, Frankfurt am Main, Fed. Rep. of Germany

[21] Appl. No.: 594,366

[22] Filed: Mar. 28, 1984

Related U.S. Application Data

[63] Continuation-in-part of Ser. No. 300,434, Sep. 8, 1981, abandoned.

[30] Foreign Application Priority Data

Sep. 10, 1980 [DE] Fed. Rep. of Germany ....... 3034001

[51] Int. Cl.$^4$ ................ C07D 401/04; A61K 31/495
[52] U.S. Cl. ................ 544/363; 260/244.4; 514/218; 514/253
[58] Field of Search ......................... 544/363

[56] References Cited

U.S. PATENT DOCUMENTS

| | | | |
|---|---|---|---|
| 3,517,005 | 6/1970 | Cronin et al. | 546/143 |
| 3,652,570 | 3/1972 | Gittos et al. | 544/363 |
| 3,932,412 | 1/1976 | Simpson et al. | 544/363 |
| 3,975,524 | 8/1976 | Nickl et al. | 544/59 |
| 4,260,611 | 4/1981 | Bartmann et al. | 544/363 |
| 4,282,222 | 8/1981 | Bartmann et al. | 544/363 |
| 4,282,223 | 8/1981 | Bartmann et al. | 544/363 |

FOREIGN PATENT DOCUMENTS

| | | | |
|---|---|---|---|
| 2030675 | 2/1971 | Fed. Rep. of Germany | 546/143 |
| 2420012 | 5/1979 | Fed. Rep. of Germany | 544/62 |
| 2503961 | 7/1979 | Fed. Rep. of Germany | 544/62 |

OTHER PUBLICATIONS

Neumeyer, J. et al., Chem. Abst. 74:99899n.
Simpson, W. et al., Chem. Abst. 80:30697b.
Chemical Abstracts, Volume 80 (1974) 306976.

*Primary Examiner*—George F. Lesmes
*Assistant Examiner*—S. A. Gibson
*Attorney, Agent, or Firm*—Curtis, Morris & Safford

[57] ABSTRACT

New isoquinoline derivatives of the general formula

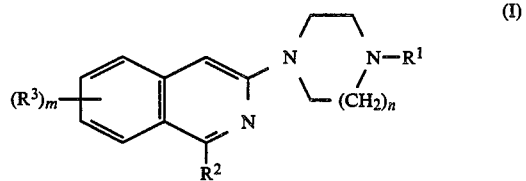

and their physiologically acceptable salts, which exert pharmacological actions on the central nervous system and the heart circulation system, a process for the preparation of these compounds, medicaments containing them, and their use as neuroleptic, antihypertonic and antiarrhythmic agents, are described.

13 Claims, No Drawings

ISOQUINOLINE COMPOUNDS

This is a continuation-in-part-application of U.S. patent application Ser. No. 300,434 filed Sept. 8, 1981 by Konz et al, now abandoned.

3-Dialkylaminoalkylamino isoquinolines are described in the literature (J. Med. chem. 13, (1970), 999–1002), but no biological effects have been described. 3,4-Dihydroisoquinolines having basic side chains in the 1-position of the isoquinoline ring possess antiarrhythmic properties (Belgian Pat. No. 764,133 and German Pat. No. 2,102,794).

Isoquinolines which have basic substituents in the 3-position and which exert valuable pharmacological actions on the central nervous system have been found.

The invention relates to isoquinoline compounds of the general formula I

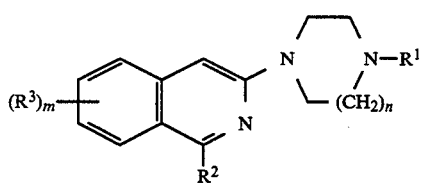

in which m denotes one or two, n denotes one or two, $R^1$ denotes (a) hydrogen, (b) straight-chain or branched $C_1$–$C_6$-alkyl, optionally substituted by hydroxyl, $C_1$–$C_4$-alkoxy or $C_3$–$C_6$-cycloalkyl, (c) thienyl, furyl, pyridiyl or pyrimidyl, (d) formyl or $C_1$–$C_6$-alkoxycarbonyl, (e) phenyl, which can be monosubstituted, disubstituted or trisubstituted by $C_1$–$C_6$-alkyl, $C_1$–$C_6$-alkoxy, methylenedioxy, hydroxyl, nitro, amino, trifluoromethyl or halogen, (f) —$(CH_2)_q$—$COR^4$, in which q is 0, 1, 2, 3 or 4 and $R^4$ is thienyl, furyl, pyridyl or an optionally substituted phenyl radical as indicated under (e), and (g)

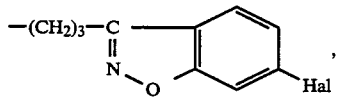

in which Hal denotes halogen; $R^2$ denotes hydrogen or $C_1$–$C_6$-alkyl, and $R^3$ denotes hydrogen, halogen, hydroxyl, $C_1$–$C_6$-alkyl, $C_1$–$C_6$-alkoxy, benzyloxy, methylenedioxy, ethylenedioxy, nitro or amino, and to salts thereof with physiologically acceptable acids.

Suitable physiologically acceptable acids are inorganic acids, such as hydrochloric acid, sulfuric acid, phosphoric acid or hydrobromic acid, or organic acids, such as formic acid, acetic acid, lactic acid, citric acid, tartaric acid, oxalic acid, maleic acid, fumaric acid, methanesulfonic acid, 1,8-naphthalenedisulfonic acid, glutaric acid or glucuronic acid.

The invention also relates to a process for the preparation of the compounds, pharmaceutical formulations and the use of the compounds.

Preferred compounds of the formula I are those in which $R^1$ denotes hydrogen, $C_1$–$C_6$-alkyl, a phenyl radical which can be monosubstituted or disubstituted by $C_1$–$C_4$-alkyl, $C_1$–$C_4$-alkoxy, methylenedioxy, hydroxyl, trifluoromethyl or halogen, in particular fluorine, chlorine or bromine, or the radical —$(CH_2)_q$—$COR^4$ in which q is 0 or 3 and $R^4$ denotes a furyl radical or a phenyl radical which is optionally substituted as indicated above under $R^1(e)$, or the radical

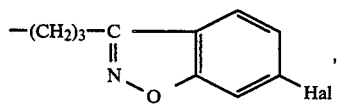

Hal representing halogen, in particular fluorine, chlorine or bromine, and in which $R^2$ denotes hydrogen or $C_1$–$C_4$-alkyl and $R^3$ denotes hydrogen, halogen, in particular fluorine, chlorine or bromine, hydroxyl, $C_1$–$C_4$-alkyl or $C_1$–$C_4$-alkoxy in the 6-position and/or 7-position. In these definitions of the substituents of the preferred compounds, $C_1$–$C_4$-alkyl denotes in each case methyl, ethyl, n-propyl, i-propyl, n-butyl, i-butyl and tert.-butyl, and $C_1$–$C_4$-alkoxy denotes the corresponding oxygen-containing radicals.

The process for the preparation of the isoquinoline compounds of the formula I comprises (a) reacting a compound of the formula II

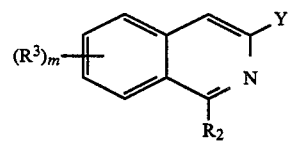

in which Y is halogen, preferably chlorine or bromine, or alkyloxy or alkylthio, each of which has 1–4 C atoms in the alkyl radical, preferably methoxy or methylthio, and $R^2$, $R^3$ and m have the meanings mentioned for the formula I, with an amine of the formula III

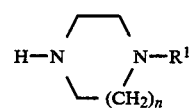

in which $R^1$ and n have the meanings mentioned for the formula I, (b) reacting a compound of the formula IV

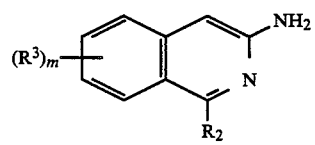

in which $R^2$, $R^3$ and m have the meanings mentioned for the formula I, with a compound of the formula V

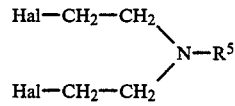

in which Hal denotes halogen, preferably chlorine or bromine, and $R^5$ denotes hydrogen, $C_1$–$C_6$-alkyl or a radical as indicated in formula I under $R^1(c)$ or $R^1(e)$, or (c) reacting a compound of the formula Ia

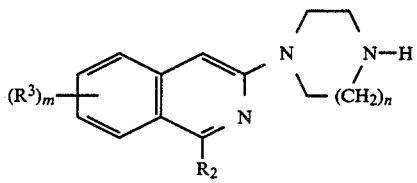

(Ia)

in which $R^2$, $R^3$, m and n have the meanings mentioned for the formula I, with an alkylating agent of the formula $Z-R^6$ in which Z denotes iodine, chlorine or bromine and $R^6$ denotes an alkyl radical as indicated in formula I under $R^1b$, or with a chloroformic acid ester of the formula $Cl-CO_2-(C_1-C_6)$-alkyl or with a compound of the formula $Cl-(CH_2)_q-COR^4$ in which $R^4$ and q have the meanings mentioned for the formula I under $R^1(f)$.

In procedure (a) it is appropriate to add at least two equivalents of amine, since one equivalent of amine is consumed to bind the hydrogen halide liberated. To accelerate the reaction it can be advantageous to use up to a 15-fold excess of the amine. On the other hand, if equimolar quantities of amine are used in the reaction it is appropriate to add a tertiary amine, such as pyridine, picoline, lutidine or 1,4-diazabicyclo-[5.4.0]-undec-5-ene, or inorganic bases, such as sodium carbonate, potassium carbonate or calcium carbonate, as an acid acceptor.

If liquid amines are used as the acid acceptor, it is possible to dispense with the addition of solvents. Suitable solvents, insofar as they are used for the reaction, are inert, anhydrous organic solvents, such as ethylene glycol monoethyl ether, octanol, diethylene glycol dimethyl ether, diethylene glycol dibutyl ether, toluene, xylene, chlorobenzene, dichlorobenzene, trichlorobenzene, dimethylformamide, dimethyl sulfoxide or hexamethylphosphoric acid triamide.

The reaction is generally carried out at a temperature between 80° and 220°, preferably between 120° and 180°.

The starting compounds of the formula II can be prepared in accordance with known methods by reducing isoquinoline derivatives analogous to formula II which are substituted by halogen in the 1-position and 3-position, using phosphorus and hydriodic acid in glacial acetic acid, or, if appropriate, by alkylation with an appropriate organometallic compound (compare, for example, S. Gabriel, Ber. 19, 2354 and Chem. pharm. Bl. (Japan) 15 (1967), 704).

In accordance with process b), amino compounds of the formula IV are subjected to a condensation reaction with N-(bis-halogenoethyl)-anilines of the formula V. The reaction is appropriately carried out in a polar solvent, such as an alcohol having 4 to 8 C atoms, for example isoamyl alccohol, or an ether, such as diethylene glycol dimethyl ether, or in an aprotic solvent, such as acetonitrile or dimethylformamide, at a temperature between 60° and 200° C., preferably 80° and 140° C., in the presence of an acid acceptor.

The starting compounds IV and V for process (b) are prepared in accordance with known methods (for example J. org. Chem. 27, 3953, (1962), J. Pharm. Soc. Japan 73, 1110 (1953) and J. Pharm. Soc. Japan 86 (1966) 544–547).

In accordance with process (c), compounds of the formula I in which $R_1$ is hydrogen and which have been prepared by process (a) or (b) are alkylated with an alkylating agent $Z-R^6$, appropriately in the presence of an acid acceptor and an organic solvent.

The alkylation with a compound of the formula $Cl-(CH_2)_q-COR^4$ can be effected advantageously in cases where q=2, 3 or 4, by means of a corresponding ketal of of the formula

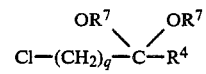

in which $R^7$ is $C_1-C_4$-alkyl, $-(CH_2)_2-$ or $-(CH_2)_3-$. The ketone is then liberated again by hydrolysis with a dilute acid, such as, for example, hydrochloric acid, sulfuric acid or acetic acid.

The compounds, according to the invention, of the formula I exhibit psychotropic actions, in particular antidepressive action—especially compounds of formula I, in which $R^1$ is hydrogen or alkyl—, or they exhibit neuroleptic action—especially compounds of formula I, in which $R^1$ is $-(CH_2)_q-COR^4$ or

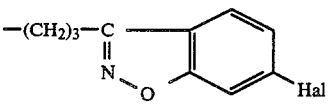

With regard to the antidepressive action, for example, the compounds of Examples 2, 3, 5, 12 and 36 to 44 were tested as serotonin agonists which are potential antidepressants. They intensify the pharmacological action of 5-hydroxytryptophane(5-HTP), a serotonin precursor. In a method modified according to CORNE et al., British J. Pharmacol, 20, 106–120 (1963), D, L-5-HTP is injected to mice in a dose provoking only a little serotonin activity in the form of isolated head twitches (200 mg/kg i.p.:n=9). The action of this threshold dose of 5-HTP is potentiated by a pretreatment with serotonin agonists. On administration of 5-HTP, the twitches are registered semiquantitatively over a period of 60 minutes and the dose is determined graphically which exceeds the effect of the control group by 200% ($ED_{+200}$).

In these test the above given compounds intensify the 5-HTP action.

With regard to the neuroleptic action, for example, the compounds of Examples 20 to 27, 29, 31 and 32 antagonize, to an extent depending on the dose, amphetamine aggregation toxicity in mice. In this test, groups of 10 mice, sitting together in a narrow space (approx. 25 cm2/mouse), receive 20 mg/kg of D-amphetamine, injected subcutaneously as a 0.2% strength aqueous solution, one hour after a compound of the formula I has been administered to them. This determines the dose of the compound I which protects 50% of the animals from death caused by amphetamine poisoning. The $ED_{50}$ values of the compounds of the formula I are between 2.0 and 40 mg/kg. These compounds of the formula I also inhibit the binding of spiroperidol labelled with tritium to cell membrane constituents composed of a homogenisate of dopamine-rich brain areas (Corpus striatum) of rats and calves ($^3$H-spiroperidol binding test, J. Z. Fields et al., Brain Research 136, 578 (1977)). The concentrations of the compounds I which are required for 50% inhibition are between 0.01 and 0.1 mmole. The compounds have only a slight cataleptogenic action, or none at all, that is to say only in high doses (>80 mg/kg) do they cause cataleptic rigidity in rats.

The compounds according to the invention, consequently, can be used for the treatment of schizophrenia or depression either on their own or mixed with physiologically acceptable auxiliaries or excipients in pharmaceutical compositions. They can be administered orally, parenterally or intravenously. For an oral administration form, a compound of the formula I is mixed with conventional pharmaceutical substances and brought, by conventional methods, into suitable administration forms, such as tablets, dry-filled capsules, aqueous, alcoholics or oily suspensions or aqueous, alcoholic or oily solutions. Examples of inert excipients which can be used are magnesium carbonate, lactose or maize starch, with the addition of other substances, such as, for example, magnesium stearate. The product can be formulated either as dry granules or moist granules. Suitable oily excipients or solvents are, in particular, vegetable oils, such as, for example, sunflower oil or olive oil.

Examples of solvents for the salts, with physiologically acceptable acids, of the compounds of the formula I which are suitable for intravenous administration are water, physiological saline solution or mixtures of water and alcohols, such as ethanol, propanediol or glycerol, and also appropriately isotonic sugar solutions, such as, for example, solutions of glucose or mannitol, or a mixture of the various solvents mentioned.

The compounds according to the invention and their pharmacologically acceptable salts are effective within a broad dosage range. The level of the dose administered depends on the type of treatment desired, on the mode of administration and on the condition, type and size of the mammal to be treated. In the case of oral administration, satisfactory results are achieved with doses of 0.1–100 mg of a compound of the formula I per kg of animal body weight. In the case of humans, the daily dose varies between 20 and 800 mg, preferably between 50 and 500 mg, it being possible to administer individual doses of 20–200 mg, preferably once to three times per day. For intravenous or intramuscular administration, the dose is 5–300 mg/day, preferably 10–200 mg/day.

In particular, the following dosages are preferred: as an anti-depressive agent, 50–100 mg per day are injected intravenously or 500–1,000 mg per day are administered perorally to an adult person (body weight 70 kg).

As a neuroleptic agent, an individual dose of 25–100 mg is administered perorally or 25–50 mg are injected intravenously to an adult. The daily peroral dose is 75–500 mg.

PROCESS (A)

EXAMPLE 1

3-(4-Methylpiperazin-1-yl)-isoquinoline 6.5 g of 3-chloroisoquinoline in 30 ml of N-methylpiperazine are boiled under reflux for 48 hours. The reaction mixture is cooled and partitioned between water and toluene, the toluene phase is washed thoroughly with water and, after drying, the solvent is removed in vacuo. The residue is recrystallized from diisopropyl ether, giving 3.8 g of 3-(4-methylpiperazin-1-yl)-isoquinoline, melting point 93°–94° C.; the dihydrochloride decomposes at 255°–257° C.

EXAMPLE 2

3-(Piperazin-1-yl)-isoquinoline 2.0 g of 3-chloroisoquinoline are boiled under reflux for 120 hours with 20 g of piperazine in 100 ml of diethylene glycol dimethyl ether. Working up as in Example 1 gives 2.4 g of 3-(piperazin-1-yl)-isoquinoline, melting point 95°–96°; its hydrochloride decomposes at 266°–268° C.

EXAMPLE 3

3-(4-(2-Hydroxyethyl)-piperazin-1-yl)-isoquinoline

Prepared analogously to Example 1 from 3-chloroisoquinoline and N-(2-hydroxyethyl)-piperazine. Melting point of base 134°–136° C.; melting point of dihydrochloride 282°–283° C.

The 3-substituted isoquinolines of the examples in Table 1 are prepared as above from the 3-chloroisoquinolines and the corresponding bases.

TABLE 1

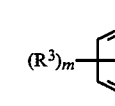

| Example | m | n | R¹ | R² | R³ | Melting point °C./ salt (Melting point °C.) |
|---|---|---|---|---|---|---|
| 4 | 1 | 1 | (2-pyridyl) | H | H | 168–170°/2 HCl (253–256°) |
| 5 | 1 | 1 | H | H | 7-OCH₃ | Oil/HCl (248–251°) |

TABLE 1-continued (R³)ₘ—[isoquinoline ring]—N(piperazine)N—R¹, (CH₂)ₙ, R₂  (I)

| Example | m | n | R¹ | R² | R³ | Melting point °C./ salt (Melting point °C.) |
|---|---|---|---|---|---|---|
| 6 | 1 | 1 | 2-methoxyphenyl | H | H | 112–114°/HCl (135–147°) |
| 7 | 1 | 1 | —CH₃ | H | 6-OCH₃ | 102–104°/HCl (256–258°) |
| 8 | 1 | 1 | H | —C₄H₉ | H | Oil/HCl (160–164°) |
| 9 | 1 | 1 | H | CH₃ | H | Oil/HCl (252–255°, decomposition) |
| 10 | 1 | 1 | pyrimidin-2-yl | H | H | 140–2°/2 HCl (252–255°) |
| 11 | 1 | 1 | H | H | 6-OCH₃ | 130–135°/HCl (220–228°, decomposition) |
| 12 | 1 | 2 | H | H | H | Oil/HCl (202–204°) |
| 13 | 1 | 1 | CH₂-(3,4-methylenedioxyphenyl) | H | H | 132–134°/HCl (234–236°) |
| 14 | 1 | 1 | H | H | 7-Cl | 112–114°/HCl (318–320°) |
| 15 | 1 | 1 | H | H | 7-OC₄H₉ | Oil/HCl (234–235° C.) |
| 16 | 1 | 1 | H | H | 7-OH | Oil/HCl (above 300° C.) |
| 17 | 1 | 1 | H | H | 7-F | Oil/HCl (252–256° C.) |
| 18 | 1 | 1 | H | H | 6,7-di-OCH₃ | Oil/HCl (220–230° C., decomposition) |

PROCESS (B)

EXAMPLE 19

3-(4-(2-Methoxyphenyl)-piperazin-1-yl)-isoquinoline

A mixture of 1.44 g of 3-aminoisoquinoline, 2.5 g of bis-N,N-(2-chloroethyl)-2-methoxyaniline, 5 g of anhydrous potassium carbonate and 30 ml of dimethylformamide is heated at 130° C. for 10 hours. After cooling, the mixture is diluted with water and extracted with methylene chloride and the solvent is removed in vacuo. 1.3 g of the base of melting point 112°–114° C. are isolated; this is identical in its properties with the compound described in Example 6.

The compounds of Examples 1–18 are also prepared in accordance with process (b) using corresponding starting materials; their fixed points are as indicated above.

EXAMPLE 1(B)

3-(4-Methylpiperazin-1-yl)-isoquinoline is prepared from 3-aminoisoquinoline and bis-N,N-(2-chloroethyl)-methylamine.

EXAMPLE 2(B)

3-(Piperazin-1-yl)-isoquinoline is prepared from 3-aminoisoquinoline and bis-2-chloroethylamine.

EXAMPLE 3(B)

3-(4-(2-Hydroxyethyl)-piperazin-1-yl)-isoquinoline is prepared from 3-aminoisoquinoline and bis-N,N-(2-chloroethyl)-2-hydroxyethylamine.

EXAMPLE 4(B)

3-(4-(2-Pyridyl)-piperazin-1-yl)-isoquinoline is prepared from 3-aminoisoquinoline and bis-N,N-(2-chloroethyl)-2-pyridylamine.

EXAMPLE 5(B)

7-Methoxy-3-(piperazin-1-yl)-isoquinoline is prepared from 7-methoxy-3-aminoisoquinoline and bis-2-chloroethylamine.

EXAMPLE 6(B)

3-(4-(2-Methoxyphenyl)-piperazin-1-yl)-isoquinoline is prepared from 3-aminoisoquinoline and bis-N,N-(2-chloroethyl)-2-methoxyaniline. (Compare Example 19).

EXAMPLE 7(B)

6-Methoxy-3-(4-methylpiperazine-1-yl)-isoquinoline is prepared from 6-methoxy-3-aminoisoquinoline and bis-N,N-(2-chloroethyl)-methylamine.

EXAMPLE 8(B)

1-Butyl-3-(piperazin-1-yl)-isoquinoline is prepared from 3-amino-1-butylisoquinoline and bis-N,N-2-chloroethylamine.

EXAMPLE 9(B)

1-Methyl-3-(piperazin-1-yl)-isoquinoline is prepared from 3-amino-1-methylisoquinoline and bis-N,N-2-chloroethylamine.

EXAMPLE 10(B)

3-(4-(2-Pyrimidinyl)-piperazin-1-yl)-isoquinoline is prepared from 3-aminoisoquinoline and bis-N,N-(2-chloroethyl)-2-pyrimidinylamine.

EXAMPLE 11(B)

6-Methoxy-3-(piperazin-1-yl)-isoquinoline is prepared from 3-amino-6-methoxyisoquinoline and bis-N,N-2-chloroethylamine.

EXAMPLE 12(B)

3-(1,4-Diazacycloheptan-1-yl)-isoquinoline is prepared from 3-aminoisoquinoline and 2-chloroethyl-3-chloropropylamine.

EXAMPLE 13(B)

3-(4-(3,4-Dioxymethylenebenzyl)-piperazin-1-yl)-isoquinoline is prepared from 3-aminoisoquinoline and bis-N,N-(2-chloroethyl)-3,4-dioxymethylenebenzylamine.

EXAMPLE 14(B)

7-Chloro-3-(piperazin-1-yl)-isoquinoline is prepared from 3-amino-7-chloro-isoquinoline and bis-N,N-2-chloroethylamine.

EXAMPLE 15(B)

7-Butoxy-3-(piperazin-1-yl)-isoquinoline is prepared from 3-amino-7-butoxy-isoquinoline and bis-N,N-2-chloroethylamine.

EXAMPLE 16(B)

7-Hydroxy-3-(piperazin-1-yl)-isoquinoline is prepared from 3-amino-7-hydroxyisoquinoline and bis-N,N-2-chloroethylamine.

EXAMPLE 17(B)

7-Fluoro-3-(piperazin-1-yl)-isoquinoline is prepared from 3-amino-7-fluoroisoquinoline and bis-N,N-2-chloroethylamine.

EXAMPLE 18(B)

6,7-Dimethoxy-3-(piperazin-1-yl)-isoquinoline is prepared from 3-amino-6,7-dimethoxy-isoquinoline and bis-N,N-2-chloroethylamine.

PROCESS (C)

EXAMPLE 20

3-(4-(3-(4-Fluorobenzoyl)-propyl)-piperazin-1-yl)-isoquinoline 6.4 g of 3-(piperazin-1-yl)-isoquinoline, prepared in accordance with Example 2 (process (a) or 2(b), process (b), 13.5 g of ω-chloro-4-fluorobutynophenone ethylene ketal, 10.6 g of sodium carbonate and 1 g of sodium iodide in 100 ml of dimethylformamide are heated at 90°–100° C. for 4 hours. The reaction mixture is cooled and partitioned between chloroform and water. The chloroform phase is extracted several times with water and the solvent is then evaporated in vacuo. The residue is dissolved in 100 ml of ethanol and boiled with 150 ml of half-concentrated hydrochloric acid. After the alcohol has been removed in vacuo, the solution is rendered alkaline with dilute sodium hydroxide solution and is extracted with chloroform.

4.6 g of 3-(4-(3-(4-fluorobenzoyl)-propyl)-piperazin-1-yl)-isoquinoline, melting point 148°–150° C., are isolated from the combined chloroform extracts. Melting point of the hydrochloride 215°–218° C.

EXAMPLE 21

3-(4-[3-(2,4-Difluorobenzoyl)-propyl]-piperazin-1-yl)-isoquinoline, melting point 122°–124° C., melting point of hydrochloride 240°–242° C., is prepared from 3-(piperazin-1-yl)-isoquinoline and ω-chloro-2,4-difluorobutyrophenone ethylene ketal.

EXAMPLE 22

7-Methoxy-3-(4-[3-(4-fluorobenzoyl)-propyl]-piperazin-1-yl)-isoquinoline, melting point 182°–185° C., melting point of hydrochloride 198°–200° C., is prepared from 7-methoxy-3-(piperazin-1-yl)-isoquinoline and ω-chloro-4-fluorobutyrophenone ethylene ketal.

EXAMPLE 23

7-Chloro-3-(4-(3-(4-fluorobenzoyl)-propyl)-piperazin-1-yl)-isoquinoline, an oil, melting point of hydrochloride 198°–202° C., is prepared from 7-chloro-3-(piperazin-1-yl)-isoquinoline and ω-chloro-4-fluorobutyrophenone ethylene ketal.

EXAMPLE 24

1-Methyl-3-(4-([3-(4-fluorobenzoyl)-propyl]-piperazin-1-yl)-isoquinoline, melting point 112°–115° C., melting point of hydrochloride 250°–254° C., is prepared from 2-methyl-3-(piperazin-1-yl)-isoquinoline and ω-chloro-4-fluorobutyrophenone ethylene ketal.

EXAMPLE 25

3-(4-(3-(4-Fluorobenzoyl)-propyl)-diazacycloheptan-1-yl)-isoquinoline, an oil, melting point of hydrochloride 206°–208° C., is prepared from 3-(4-diazacycloheptan-1-yl)-isoquinoline and ω-chloro-4-fluorobutyrophenone ethylene ketal.

EXAMPLE 26

3-(4-(3-(2-Nitro-4-fluorobenzoyl)-propyl)-piperazin-1-yl)-isoquinoline, melting point 103°–105° C., is prepared from 3-(piperazin-1-yl)-isoquinoline and ω-chloro-2-nitro-4-fluorobutyrophenone ethylene ketal.

EXAMPLE 27

3-(4-(3-(2-Amino-4-fluorobenzoyl)-propyl)-piperazin-1-yl)-isoquinoline 1.7 g of 3-(3-(4-(2-nitro-4-fluorobenzoyl)-propyl)-piperazin-1-yl)-isoquinoline (Example 26) are hydrogenated over 180 mg of 10% strength palladium-on-charcoal in 8 ml of ethanolic hydrogen chloride solution and 50 ml of methanol under normal pressure and at room temperature, until the theoretical quantity of hydrogen has been taken up. The catalyst is filtered off, the solvent is evaporated and the residue is recrystallized from ethanol. Melting point 124°–128° C., melting point of hydrochloride 220°–223° C.

EXAMPLE 28

3-(4-[4,4-bis-(4-Fluorophenyl)-butyl]-piperazin-1-yl)-isoquinoline 5.0 g of 3-(piperazin-1-yl)-isoquinoline, 11.4 g of 4-bis-(4-fluorophenyl)-butyl bromide, 6.4 g of potassium carbonate and 0.2 g of potassium iodide in 140 ml of dimethylformamide are warmed at 90° C. for 4 hours. After cooling, the mixture is partitioned between water and chloroform and the chloroform phase is dried and concentrated on a rotary evaporator. The residue crystallizes (4.8 g) from ethanol, melting point 116°–118° C., melting point of hydrochloride 176°–178° C.

EXAMPLE 29

3-(4-(3-(5-Fluorobenzisoxazol-3-yl)-propyl)-piperazin-1-yl)-isoquinoline (a) 1.2 g of 3-(4-(3-(2,4-difluorobenzoyl)-propyl)-piperazin-1-yl)-isoquinoline, 1.2 g of ammonium acetate, 0.6 g of hydroxylamine hydrochloride in 15 ml of methanol and 4 ml of water are boiled under reflux for 2½ hours. After cooling, the mixture is diluted with water and extracted with chloroform. 0.85 g of oxime, melting point 144°–146° C., is isolated.

(b) 0.8 g of the oxime described above, in 15 ml of DMF and 8 ml of THF, is added dropwise slowly at room temperature to 0.25 g of 50% strength sodium hydride in 20 ml of tetrahydrofuran. After 6 hours, the suspension is then stirred at 80°–90° C. and is then hydrolyzed with water. The solution is partitioned between saturated sodium chloride solution and ether. 0.1 g crystallizes from the ether solution, melting point 130°–133° C., melting point of hydrochloride 172°–174° C.

EXAMPLE 30

3-(4-(4-Methoxybenzoyl)-piperazin-1-yl)-isoquinoline 9.38 g of 4-methoxybenzoyl chloride are added dropwise to 10 g of 3-(piperazin-1-yl)-isoquinoline, dissolved in 40 ml of pyridine. After stirring for 1 hour at room temperature, the mixture is diluted with water and extracted with ethyl acetate. The ethyl acetate phase is dried and the solvent is removed by evaporation. 5.8 g, melting point 156°–159° C., can be isolated.

The following compounds are prepared analogously:

EXAMPLE 31

7-Butoxy-3-(4-(3-(4-fluorobenzoyl)-propyl)-piperazine-1-yl)-isoquinoline, melting point 157°–159° C., is prepared from 7-butoxy-3-(piperazin-1-yl)-isoquinoline and ω-chloro-4-fluorobutyrophenone ethylene ketal.

EXAMPLE 32

7-Fluoro-3-(4-(3-(4-fluorobenzoyl)-propyl)-piperazin-1-yl)-isoquinoline, is prepared from 7-fluoro-3-(piperazin-1-yl)-isoquinoline and ω-chloro-4-fluorobutyrophenone ethylene ketal. Melting point of hydrochloride 212°–217° C.

EXAMPLE 33

3-(4-(3-(2-Thienoyl)-propyl)-piperazin-1-yl)-isoquinoline is prepared from 3-(piperazin-1-yl)-isoquinoline and ω-chloro-2-thienyl propyl ketone ethylene ketal. Melting point 94°–100° C.; melting point of hydrochloride 254°–260° C.

EXAMPLE 34

3-(4-(3-(4-Bromobenzoyl-propyl)-piperazin-1-yl)-isoquinoline is prepared from 3-(piperazin-1-yl)-isoquinoline and ω-chloro-4-bromobutyrophenone ehtylene ketal. An oil, melting point of hydrochloride 250°–254° C.

EXAMPLE 35

3-(4-(3-Benzoylpropyl)-piperazin-1-yl)-isoquinoline is prepared from 3-(piperazin-1-yl)-isoquinoline and ω-chloro-3-benzoylpropyl ethylene ketal. An oil, melting point of hydrochloride 277°–278° C.

In analogy to Example 1 the following compounds were obtained:

EXAMPLE 36

6,7-Dimethyl-3-(piperazin-1-yl)-isoquinoline hydrochloride M.P. 272°–276° C.

EXAMPLE 37

5,7-Dimethyl-3-(piperazin-1-yl)-isoquinoline hydrochloride M.P. 260° C.

EXAMPLE 38

5,8-Dimethyl-3-(piperazin-1-yl)-isoquinoline hydrochloride M.P. 260° C.

EXAMPLE 39

5,6-Dimethyl-3-(piperazin-1-yl)-isoquinoline hydrochloride M.P. 260° C.

EXAMPLE 40

6,7-Diethyl-3-(piperazin-1-yl)-isoquinoline hydrochloride M.P. 264° C.

EXAMPLE 41

7,8-Dimethyl-3-(piperazin-1-yl)-isoquinoline hydrochloride M.P. 224°–227° C.

EXAMPLE 42

5,8-Diethyl-3-(piperazin-1-yl)-isoquinoline hydrochloride M.P. 160°–163° C.

EXAMPLE 43

6,8-Dimethyl-3-(piperazin-1-yl)-isoquinoline hydrochloride M.P. 214°–217° C.

EXAMPLE 44

7,8-Dimethyl-3-(4-(2-hydroxyethyl)-piperazin-1-yl)-isoquinoline hydrochloride. M.P. 255°–258° C.

We claim:

1. An isoquinoline compound of the general formula I

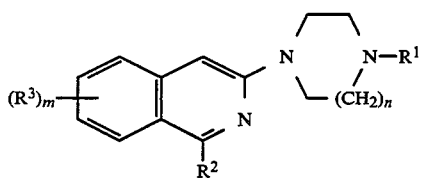 (I)

in which m denotes one, n denotes one or two R[1] denotes (a) hydrogen, (b) methyl or ethyl, (c) —(CH$_2$)$_q$—COR$^4$, in which q is 3, and R$^4$ is thienyl, phenyl or a phenyl radical monosubstituted or disubstituted by nitro, amino or halogen, or (d)

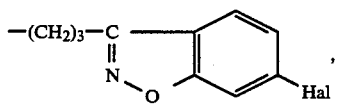, in which Hal denotes halogen; R$^2$ denotes hydrogen, methyl or ethyl, and R$^3$ denotes hydrogen, halogen, hydroxyl, methyl or ethyl, methoxy or ethoxy and a salt thereof with a physiologically acceptable acid.

2. The compound defined in claim 1 which is 3-(piperazin-1-yl)-isoquinoline.

3. The compound defined in claim 1 which is 3-(4-[3-(4-fluorobenzoyl)-propyl]-piperazin-1-yl)-isoquinoline.

4. The compound defined in claim 1 which is 7-methoxy-3-(4-[3-(4-fluorobenzoyl)-propyl]-piperazin-1-yl)-isoquinoline.

5. The compound defined in claim 1 which is 3-(4-[3-(2-amino-4-fluorobenzoyl)-propy]-piperazin-1-yl)-isoquinoline.

6. The compound which is 3-(4-[3-(5-fluorobenzisoxazol-3-yl)-propyl]-piperazin-1-yl)-isoquinoline.

7. The compound defined in claim 1 which is 3-(4-[3-(4-bromobenzoyl)-propyl]-piperazin-1-yl)-isoquinoline.

8. The compound defined in claim 1 which is 5,8-dimethyl-3-(piperazin-1-yl)-isoquinoline.

9. The compound defined in claim 1 which is 7,8-dimethyl-3-(piperazin-1-yl)-isoquinoline.

10. The compound defined in claim 1 wherein n is 1.

11. The compound defined in claim 1 wherein R$^1$ is hydrogen, —(CH$_2$)$_q$COR$^4$ or

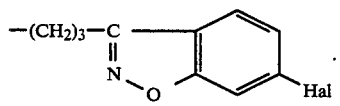

12. The compound defined in claim 1 wherein R$^1$ is

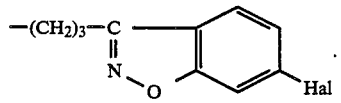

13. The compound defined in claim 1 wherein R$^2$ is hydrogen.

* * * * *

UNITED STATES PATENT AND TRADEMARK OFFICE
CERTIFICATE OF CORRECTION

PATENT NO. : 4,590,273

DATED : May 20, 1986

INVENTOR(S) : Konz et al.

It is certified that error appears in the above-identified patent and that said Letters Patent is hereby corrected as shown below:

Column 13, line 19
 (Claim 1, line 3), change "m denotes one" to --m denotes one or two-- and "n denotes one or two" to --n denotes one--.

Signed and Sealed this

Twenty-first Day of October, 1986

[SEAL]

Attest:

DONALD J. QUIGG

*Attesting Officer*   *Commissioner of Patents and Trademarks*